United States Patent [19]

Heeres et al.

[11] Patent Number: 4,916,134

[45] Date of Patent: Apr. 10, 1990

[54] 4-[4-[4-[4-[[2-(2,4-DIFLUOROPHENYL)-2-(1H-AZOLYLMETHYL)-1,3-DIOXOLAN-4-YL]METHOXY]PHENYL]-1-PIPERAZINYL]-PHENYL]TRIAZOLONES

[75] Inventors: Jan Heeres, Vosselaar; Leo J. J. Backx, Arendonk; Louis J. E. Van der Veken, Vosselaar, all of Belgium

[73] Assignee: Janssen Pharmacuetica N.V., Beerse, Belgium

[21] Appl. No.: 336,549

[22] Filed: Apr. 7, 1989

Related U.S. Application Data

[63] Continuation of Ser. No. 164,024, Mar. 4, 1988, abandoned, which is a continuation-in-part of Ser. No. 30,207, Mar. 25, 1987, abandoned.

[51] Int. Cl.$^4$ .................. A61K 31/495; C07D 403/14
[52] U.S. Cl. .................................... 514/252; 544/366; 544/370
[58] Field of Search ................. 544/366, 370; 514/252

[56] References Cited

U.S. PATENT DOCUMENTS

| 4,267,179 | 5/1981 | Heeres et al. | 424/25 |
| 4,287,195 | 9/1981 | Heeres et al. | 544/367 |
| 4,368,200 | 1/1983 | Heeres et al. | 544/370 |
| 4,404,216 | 9/1983 | Richardson | 548/262 |
| 4,490,530 | 12/1984 | Heeres et al. | 544/370 |
| 4,791,111 | 12/1988 | Heeres et al. | 514/252 |

OTHER PUBLICATIONS

Barriese, Hospital Therapy, (1988), "Iraconazole and Fluconazole", pp. 68–83.
Janssen et al., A Postgraduate Symposium: Dermatology Update, "Antifungal Therapy of the Future".

Primary Examiner—Cecilia Chen
Attorney, Agent, or Firm—Charles J. Metz

[57] ABSTRACT

4-[4-[4-[4-[[2-(2,4-difluorophenyl)-2-(1H-azolylmethyl)-1,3-dioxolan-4-yl]methoxy]phenyl]-1-piperazinyl]-phenyl]triazolones, their pharmaceutically acceptable acid addition salts and stereoisomeric forms having improved antimicrobial properties, compositions containing the same, and methods of inhibiting and/or eliminating the development of fungi and bacteria in warm-blooded animals suffering from diseases caused by these fungi and/or bacteria.

10 Claims, No Drawings

4-[4-[4-[4-[[2-(2,4-DIFLUOROPHENYL)-2-(1H-AZOLYLMETHYL)-1,3-DIOXOLAN-4-YL]METHOXY]PHENYL]-1-PIPERAZINYL]PHENYL]-TRIAZOLONES

CROSS-REFERENCE TO RELATED APPLICATION

This a continuation of application Ser. No. 164,024, filed Mar. 4, 1988, now abandoned, which is in turn continuation-in-part of our co-pending application Ser. No. 30,207 filed Mar. 25, 1987, now abandoned.

BACKGROUND OF THE INVENTION

In U.S. Pat. No. 4,267,179 there are described a number of heterocyclic derivatives of (4-phenyl-1-piperazinyl-aryloxymethyl-1,3-dioxolan-2-yl)methyl-1H-imidazoles and 1H-1,2,4-triazoles, which compounds are taught to possess antifungal and antibacterial properties.

Quite unexpectedly, it now has been found that the 2-(2,4-difluorophenyl)-1,3-dioxolan analogs of the compounds described in said U.S. Pat. No. 4,267,179 show improved antimicrobial activity, in particular against fungi belonging to the genus Aspergillus.

DESCRIPTION OF THE INVENTION

This invention is concerned with 1H-imidazoles and 1H-1,2,4-triazoles having the formula

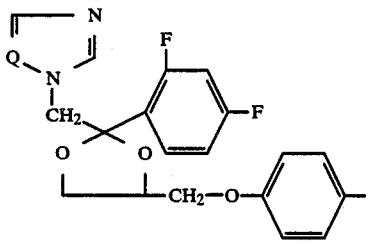

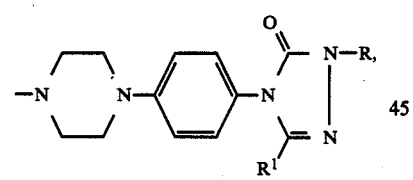

the pharmaceutically acceptable acid addition salts and the stereochemically isomeric forms thereof, wherein
Q is N or CH;
R is hydrogen, $C_{1-6}$alkyl or aryl$C_{1-6}$alkyl; and
$R^1$ is hydrogen, $C_{1-6}$alkyl or aryl$C_{1-6}$alkyl;
wherein aryl is phenyl optionally substituted with up to 3 substituents each independently selected from halo, $C_{1-6}$alkyl, $C_{1-6}$alkyloxy and trifluoromethyl.

In the foregoing definitions the term "halo" is generic to fluoro, chloro, bromo and iodo and the term "$C_{1-6}$ alkyl" is meant to include straight and branched hydrocarbon radicals having from 1 to 6 carbon atoms such as for example, methyl, ethyl, propyl, 1-methylethyl, 1,1-dimethylethyl, 1-methylpropyl, 2-methylpropyl, butyl, pentyl, hexyl and the like.

The compounds of formula (I) wherein R is hydrogen contain in their structure a tautomeric system and consequently these compounds can be present in each of their tautomeric forms, both of which are intended to be included within the scope of the present invention.

The compounds of formula (I) may also exist in hydrated or in solvent addition forms and said forms are intended to be included within the scope of the present invention.

Preferred compounds within the present invention are those compounds of formula (I) wherein R and $R^1$ independently are hydrogen or $C_{1-6}$alkyl.

More preferred compounds are those preferred compounds wherein $R^1$ is hydrogen and R is $C_{1-6}$alkyl.

Particularly preferred compounds are those more preferred compounds wherein the substituents on the dioxolane moiety have a cis configuration.

A particular subgroup of the compounds of formula (I) comprises those compounds, preferred or particularly preferred compounds wherein Q is nitrogen.

The most preferred compounds are selected from the group consisting of cis-4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(1-methylpropyl)-3H-1,2,4-triazol-3-one and cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-(1,2-dimethylpropyl)-2,4-dihydro-3H-1,2,4-triazol-3-one and the pharmaceutically acceptable salts thereof.

In order to simplify the structural representations of the compounds of formula (I) and of certain starting materials and intermediates used in the preparation thereof, the 2-(2,4-difluorophenyl)-2-(1H-imidazol-1-ylmethyl or 1H-1,2,4-triazol-1-ylmethyl)-1,3-dioxolan-4-yl group will hereafter be represented by the symbol D:

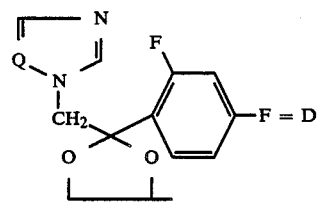

The compounds of formula (I) can be prepared by O-alkylating an appropriately substituted phenol of formula (III) with an alkylating reagent of formula (II).

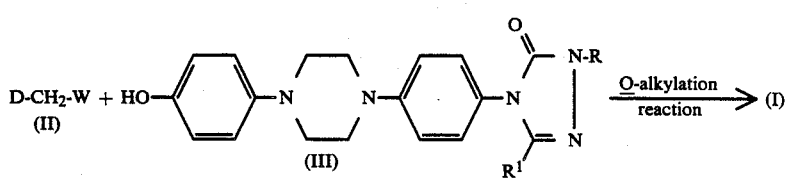

In formula (II) and in a number of the following intermediates, W represents a reactive leaving group such as, for example, halo, preferably chloro, bromo or iodo, or a sulfonyloxy group such as, for example, methylsulfonyloxy, 2-naphtalenesulfonyloxy or 4-methylphenylsulfonyloxy and the like.

The alkylation reaction of (II) with (III) can be carried out under art-known conditions of performing O-alkylations. Said O-alkylation reaction can conveniently be conducted in a suitable reaction-inert solvent in the presence of an appropriate base. A suitable reaction-inert solvent is, for example, an aromatic hydrocarbon, e.g., benzene, methylbenzene, dimethylbenzene and the like; a halogenated hydrocarbon, e.g., dichloronated hydrocarbon, e.g., trichloromethane; an alkanol, e.g., ethanol, propanol, butanol and the like, or a mixture of such solvents. Preferably, the water which is liberated during the course of the reaction, is removed by azeotropical destillation.

Or, the compounds of formula (I) may also be synthesized by N-alkylating an azole (VI) wherein Q is as defined under formula (I), with an intermediate of formula (VII) wherein $R^1$ and $R^2$ have the previously defined meaning.

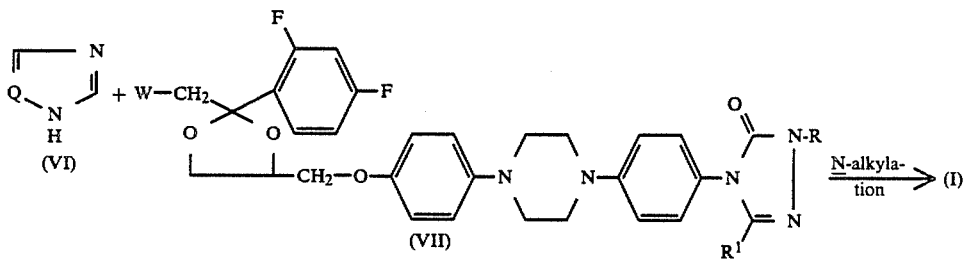

methane, trichloromethane and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g., N,N-dimethylformamide, N,N-dimethylacetamide, hexamethylphosphoric triamide, dimethyl sulfoxide, nitrobenzene, 1-methyl-2-pyrrolidinone and the like, or a mixture of said solvents. The acid which is liberated during the course of the reaction may be picked up by an appropriate base such as, for example, an alkali or an earth alkaline metal carbonate, hydrogen carbonate, hydroxide, alkoxide, hydride or amide, e.g., sodium carbonate, potassium carbonate, sodium hydroxide, sodium methoxide, sodium hydride, sodium amide and the like, or an organic base such as, for example, an amine, e.g., N,N-diethylethanamine, N-(1-methylethyl)-2-propanamine, 4-ethylmorpholine, and the like. In some instances it may be advantageous to convert the substituted phenol (III) first into a metal salt thereof, preferably the sodium salt, in the usual manner, e.g., by the reaction of (III) with a metal base such as sodium hydride, sodium hydroxide and the like, and to use said metal salt subsequently in the reaction with (II).

Alternatively, the compounds of formula (I) may be prepared following the procedures described in U.S. Pat. No. 4,101,666, which is incorporated herein by reference, for instance, by the acetalization reaction of a ketone of formula (IV) with a diol of formula (V) in the presence of an acid such as, for example, benzenesulfonic acid, 4-methylbenzenesulfonic acid, methanesulfonic acid and the like acids.

Said N-alkylation reaction can conveniently be conducted in a suitable reaction-inert solvent or a mixture of such solvents in the presence of an appropriate base. Suitable reaction-inert solvents are, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent, e.g., N,N-dimethylformamide, N,N-dimethylacetamide, dimethyl sulfoxide, nitrobenzene, 1-methyl-2-pyrrolidinone, and the like; a halogenated hydrocarbon, e.g., dichloromethane, trichloromethane and the like.

The addition of an appropriate base such as, for example, an alkali or an earth alkaline metal carbonate, hydrogen carbonate, hydroxide, amide or hydride, e.g., sodium hydroxide, potassium hydroxide, potassium carbonate, sodium hydride and the like or an organic base such as, for example, N,N-dimethyl-4-pyridinamine, N,N-diethylethanamine or N-(1-methylethyl)-2-propanamine may be employed to pick up the acid which is liberated during the course of the reaction.

In some instances it may be advantageous to use an excess of the azole (VI) or to convert it ot its metal salt form, in particular its alkali metal salt form following art-known procedures such as, e.g. by treatment of the azole (VI) with an alkali metal hydroxide, alkoxide, amide or hydride.

The compounds of formula (I) may also be obtained by cyclizing an intermediate of formula (VIII) with an appropriately substituted benzenamine of formula (IX),

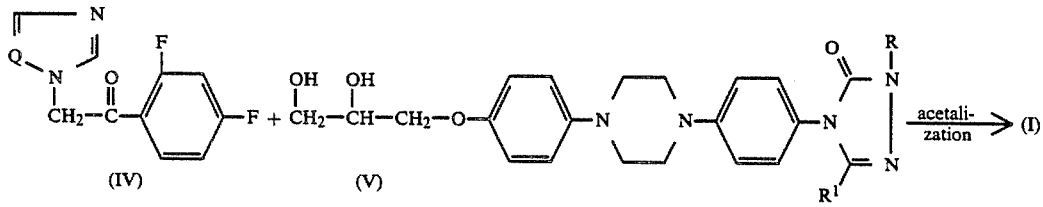

Said acetalization reaction can conveniently be conducted in a reaction-inert solvent such as, an aromatic hydrocarbon, e.g., benzene, methyl-benzene, a halogenated hydrocarbon, e.g., trichloromethane, a halogeor by cyclizing a benzenamine of formula (X) with a reagent of formula (XI).

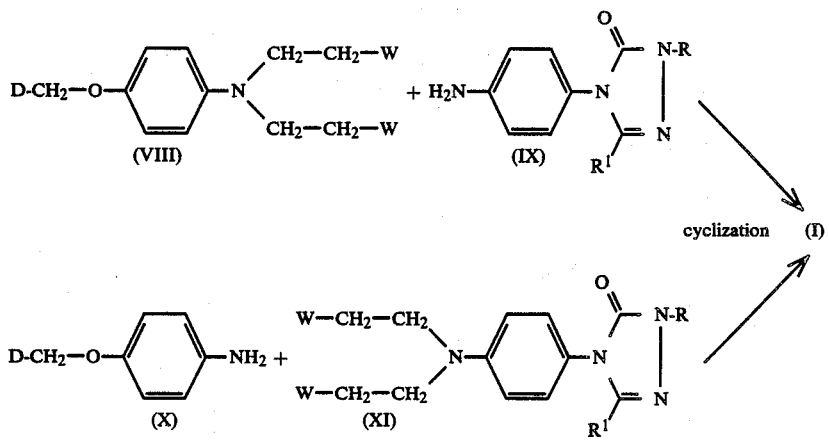

Said cyclization reaction may be carried out by stirring the reactants in the presence of an appropriate polar solvent, e.g. water, in admixture with an appropriate water-miscible organic solvent, such as, for example, 2-propanol, 2-propanone and the like, preferably at an elevated temperature and most preferably, in the presence of an alkali or earth alkaline metal iodide such as, e.g., potassium iodide.

Furthermore, the compounds of formula (I) may be prepared by N-alkylating a piperazine of formula (XII) with a benzene of formula (XIII), or by N-alkylating a piperazine of formula (XV) with a benzene of formula (XIV) following standard N-alkylating procedures. In formulae (XIII) and (XIV) $W^1$ represents an appropriate reactive leaving group, such as, for example, halo, e.g., chloro or bromo and in particular fluoro.

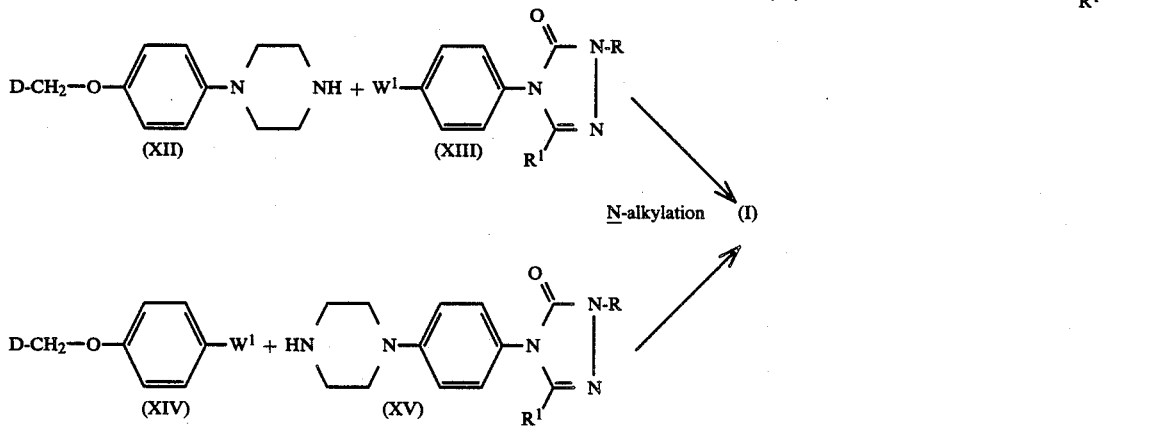

Said N-alkylation may be carried out by stirring the reactants, preferably at somewhat elevated temperatures, in an appropriate organic solvent such as, for example, N,N-dimethylformamide, N,N-dimethylacetamide, dimethyl sulfoxide and the like, in the presence of an appropriate base such as, for example, an alkali metal hydride or carbonate and the like bases.

The compounds of formula (I) wherein R is hydrogen, said compounds being represented by formula (I-a), can generally be prepared by cyclizing an intermediate of formula (XVI) with an appropriate reagent of formula (XVII).

In formula (XVII) $L^1$ and $L^2$ both represent an appropriate leaving group such as, for example, $C_{1-6}$alkyloxy, di($C_{1-4}$alkyl)amino and the like groups and $R^1$ has the previously defined meaning. Said cyclization reaction can generally be conducted in a suitable reaction-inert solvent such as, for example, an alcohol, e.g., butanol and the like; an ether, e.g., tetrahydrofuran, 1,4-dioxane, 1,1'-oxybis(2-methoxyethane); tetrahydrothiophene 1,1-dioxide and the like solvents. Although the cyclization reaction may be conducted at room temperature, somewhat elevated temperatures are appropriate to enhance the rate of the reaction. Preferably the reaction is conducted at the reflux temperature of the reaction mixture.

The compounds of formula (I-a) may alternatively be prepared by cyclizing an intermediate of formula (XVIII) with an appropriate amidine of formula (XIX) or an acid addition salt thereof.

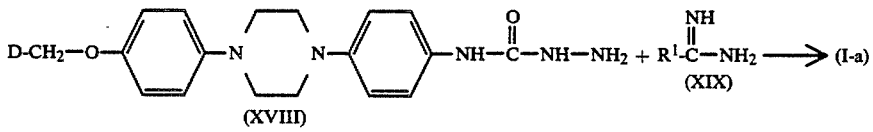

Said cyclization may be carried out by mixing and heating the reactants, preferably, in the presence of an appropriate reaction-inert organic solvent having a relatively high boiling point such as, for example, 1,1'-oxybis(2-methoxyethane).

The compounds of formula (I) wherein R is other than hydrogen, said R being represented by $R^2$ and said compounds being represented by formula (I-b), may be prepared by N-alkylating a compound of formula (I-a), with a reagent of formula (XX).

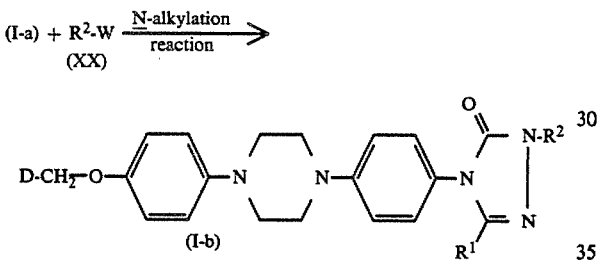

Said N-alkylation reaction may easily be performed following the same procedure as outlined for the preparation of compounds of formula (I) from (VI) and (VII). It may be advantageous however, to convert the compound of formula (I-a) first into a metal salt form thereof, preferably the sodium salt, in the usual manner, e.g., by reaction of (I-a) with a metal base such as sodium hydride, sodium hydroxide and the like bases, and to use said metal salt subsequently in the reaction with (XX). The addition of a iodide salt, preferably an alkali iodide, may be appropriate. Somewhat elevated temperatures and stirring may enhance the rate of the reaction.

The 1H-imidazole- and 1H-1,2,4-triazole-derivatives of formula (I), obtained in basic form in the foregoing preparations, may be converted to their therapeutically active non-toxic acid addition salt forms by treatment with appropriate acids, such as, for example, inorganic acids, such as hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The salts in turn are converted to the corresponding free bases in the usual manner, i.e., by reaction with alkali, for instance, sodium or potassium hydroxide.

From formula (I) it is evident that the compounds of this invention have at least two asymmetric carbon atoms in their structures namely those located in the 2- and 4-position of the dioxolane nucleus. Depending on the structure of R and/or $R^1$ further asymmetric centra may be present in said R and/or $R^1$ substituent, and consequently the compounds of formula (I) can exist under different stereochemically isomeric forms. The stereochemically isomeric forms of (I) and the pharmaceutically acceptable acid addition salts thereof are intended to be embraced within the scope of the invention.

The diastereomeric racemates of (I), denoted as cis and trans forms according to the rules described in J. Org. Chem. 35 (9), 2849–2867 (1970), may be obtained separately by conventional methods. Appropriate methods which may advantageously be employed include, for example, selective crystallization and chromatographical separation, e.g., column chromatography.

Since the stereochemical configuration is already fixed in a number of intermediate compounds, e.g., in the intermediates of formulae (II), (VII), (VIII), (X), (XII), (XIV), (XVI) and (XVIII), it is also possible to separate cis and trans forms at this or, when possible, even an earlier stage. The corresponding diastereomeric forms of (I) may be derived thereform in the previously indicated manner. The separation of cis and trans forms of such intermediates may be preformed by conventional methods as mentioned hereinabove for the separation of the cis and trans forms of the compounds of formula (I).

It is evident that the cis and trans racemates may be further resolved into their optical isomers, cis(+) and cis(−), respectively trans(+) and trans(−) by the application of methodologies known to those skilled in the art. In case additional asymmetric centra are present in the abovementioned intermediates and/or compounds, the resulting mixtures of stereoisomers may be further separated by the previously indicated methodologies. Preferably, if a specific stereochemical form is desired, said compound will be synthesized by stereoselective methods of preparation, which will advantageously employ enantiomerically pure starting materials.

A number of intermediates and starting materials used in the foregoing preparations are known compounds, others may be prepared according to art-known methodologies of preparing said or similar compounds, while still others are new. A number of such preparation methods will be described hereinafter in more detail.

The intermediates of formula (III), (XVI) and (XVIII) can conveniently be prepared following procedures analogous to those described in U.S. Pat. No. 4,267,179, which is incorporated herein by reference.

Starting materials of formula (II) may be derived from a 1-(2,4-difluorophenyl)-2-haloethanone by reacting the latter with an azole (VI) in an reaction inert solvent, if appropriate in the presence of a base, and subsequently reacting the thus obtained 1-(2,4-difluorophenyl)-2-(azole-1-yl)ethanone (IV) with 1,2,3- propanetriol in a suitable acetalizing medium. The desired alkylating reagents of formula (II) can easily by prepared by converting the remaining hydroxy group of the obtained intermediate into a reactive leaving group according to methodologies generally known in the art. Said reactive derivatives of formula (II) can alternatively be prepared according to a sequence of reactions similar to the procedures described in U.S. Pat. No. 4,267,179.

The intermediates of formula (VII) are prepared following procedures described in U.S. Pat. No. 4,101,666, which is incorporated herein by reference, e.g., by the acetalization reaction of a diol of formula (V) with a 1-(2,4-difluorophenyl)-2-haloethanone. In turn, the intermediates of formula (V) can be obtained by O-alkylating an intermediate of formula (III) with (chloromethyl)oxirane and subsequent hydrolysis of the epoxide.

The previously described intermediates and starting materials may also be converted into each other following art-known functional group transformation procedures.

The compounds of formula (I), the pharmaceutically acceptable acid addition salts and stereochemically isomeric forms thereof show antimicrobial activity and more particularly they possess superior antifungal activity. The latter activity of the compounds of formula (I) can be demonstrated in the "Topical treatment of vaginal candidosis in rats" test, "Topical treatment of microsporosis in guinea pigs" test and "Oral treatment of aspergillosis in mice" test.

In view of their useful antimicrobial activity, the subject compounds may be formulated into various pharmaceutical forms for administration purposes.

To prepare the pharmaceutical compositions of this invention, an effective amount of the particular, compound optionally in acid addition salt form, as the active ingredient is combined in intimate admixture with a pharmaceutically acceptable carrier, which carrier may take a wide variety of forms depending on the desired mode of administration. These pharmaceutical compositions are preferably in unitary dosage form suitable for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of formula (I), the pharmaceutically acceptable acid addition salts and stereochemically isomeric forms thereof are useful agents in combatting fungi and bacteria. For example, said compounds are found to be highly active against a wide variety of fungi such as, for example, *Microsporum canis, Pityrosporum ovale, Ctenomyces mentagrophytes, Trichophyton rubrum, Phialophora verrucosa, Cryptococcus neoformans, Candida tropicalis, Candida albicans, Mucor species, Aspergillus fumigatus, Sporotrichum schenckii* and *Saprolegnia species*, and against bacteria such as, for example, *Erysipelotrix insidiosa*, Staphylococci such as *Staphylococcus hemolyticus* and Streptococci such as *Streptococcus pyogenes*. In view of their potent, local as well as systemic, antimicrobial activity the compounds of this invention constitute useful tools for the destruction or prevention of the growth of fungi and bacteria and more particularly they can effectively be used in the treatment of warm-blooded animals suffering from diseases such as, for example, tinea corporis, tinea cruris, tinea manus, tinea pedis, candidosis, pityriasis versicolor, onychomycosis, perionyxis, paracoccidioidomycosis, histoplasmosis, coccidioidomycosis, cryptococcosis, chromomycosis, mucormycosis, sporotrichosis, erysipelas, staphylococcosis, seborrheic dermatitis and the like.

The compounds of the present invention are particularly attractive due to their greatly improved action against Aspergillus species and are therefore especially useful in the treatment of aspergillosis in warm-blooded animals.

Those of skill in treating warm-blooded animals suffering from diseases caused by fungi and/or bacteria could easily determine the effective amount from the test results presented here. In general it is contemplated that an effective amount would be from 0.01 mg/kg to 50 mg/kg body weight, and more preferably from 0.05 mg/kg to 20 mg/kg body weight. For topical applications it is contemplated that an effective amount would be from 0.001% to 5% (by weight) and more preferably from 0.1% to 1% (by weight).

The following examples are intended to illustrate and not to limit the scope of the present invention. Unless otherwise stated all parts therein are by weight.

EXPERIMENTAL PART

A. Preparation of intermediates

EXAMPLE 1

(a) A mixture of 200 parts of 1,2,3-propanetriol, 90 parts of 1-(2,4-difluorophenyl)-2-(1H-1,2,4-triazol-1-yl)ethanone, 600 parts of methanesulfonic acid and 190 parts of benzene was stirred first at reflux for 3 hours using a water-separator and further overnight at room temperature. The reaction mixture was added dropwise to a sodium hydrogen carbonate solution. The product was extracted with trichloromethane. The extract was washed with water, dried, filtered and evaporated. The residue was triturated in 4-methyl-2-pentanone. The product was filtered off and dried, yielding 80 parts (67.2%) of (cis+trans)-2-(2,4-difluorophenyl)-2-(1H-1,2,4-triazol-1-ylmethyl)-1,3-dioxolane-4-methanol (intermediate 1).

(b) A mixture of 69 parts of 3,5-dinitrobenzoyl chloride, 80 parts of (cis+trans)-2-(2,4-difluorophenyl)-2-(1H-1,2,4-triazol-1-ylmethyl)-1,3-dioxolane-4-methanol, 400 parts of pyridine and 520 parts of dichloromethane was stirred for 3 hours at room temperature. The reaction mixture was evaporated and the residue was taken up in water. The product was extracted with trichloromethane. The extract was dried, filtered and evaporated. The residue was purified by column chromatography over silica gel using a mixture of trichloromethane and methanol (99:1 by volume) as eluent. The pure fractions were collected and the eluent was evaporated, yielding 90 parts (70.4%) of (cis)-2-(2,4-difluorophenyl)-2-(1H-1,2,4-triazol-1-ylmethyl)-1,3-dioxolane-4-methanol 3,5-dinitrobenzoate(ester) as a residue (intermediate 2).

(c) A mixture of 90 parts of (cis)-2-(2,4-difluorophenyl)-2-(1H-1,2,4-triazol-1-ylmethyl)-1,3-dioxolane-4-methanol 3,5-dinitrobenzoate (ester), 16 parts of sodium hydroxide solution 50%, 800 parts of 1,4-dioxane and 400 parts of water was stirred overnight at room temperature. The reaction mixture was poured into water. The product was extracted with dichloromethane. The extract was washed with water, dried, filtered and evaporated. The residue was triturated in 4-methyl-2-pentanone. The product was filtered off and dried, yielding 30 parts (56.0%) of cis-2-(2,4-difluorophenyl)-2-(1H-1,2,4-triazol-1-ylmethyl)-1,3-dioxolane-4-methanol as a residue (intermediate 3).

(d) A mixture of 11.4 parts of methanesulfonyl chloride, 25 parts of cis-2-(2,4-difluorophenyl)-2-(1H-1,2,4-triazol-1-ylmethyl)-1,3-dioxolane-4-methanol, 300 parts of pyridine and 390 parts of dichloromethane was stirred for 3 hours at room temperature. The reaction mixture was evaporated and the residue was taken up in trichloromethane. The organic phase was dried, filtered and evaporated. The residue was triturated in 2,2'-oxybispropane. The product was filtered off and dried, yielding 29.4 parts (93.2%) of cis-2,4-di-fluorophenyl)-2-(1H-1,2,4-triazol-1-ylmethyl)-1,3-dioxolane-4-methanol methanesulfonate(ester) as a residue (intermediate 4).

In a similar manner there was also prepared: cis-2-(2,4-difluorophenyl)-2-(1H-imidazol-1-ylmethyl)-1,3-dioxolane-4-methanol methanesulfonate(ester) ethanedioate(1:1) (intermediate 5).

EXAMPLE 2

(a) To a stirred solution of 122.0 parts of (cis+trans)-2-(2,4-difluorophenyl)-2-(1H-1,2,4-triazol-1-ylmethyl)-1,3-dioxolane-4-methanol and 1.0 part of N,N-dimethyl-4-pyridinamine in 1300 parts of dichloromethane was added dropwise a solution of 121.2 parts of 2-naphthalenesulfonyl chloride in 100 parts of pyridine during a period of 2 hours. Upon complete additon, stirrring was continued overnight at room temperature. The reaction mixture was washed twice with water and evaporated in vacuo. The residue was purified by column chromatography over silica gel using trichloromethane as eluent. The pure fractions were collected and the eluent was evaporated. The residue was crystallized from 4-methyl-2-pentanone. The product was filtered off and dried, yielding 102.3 parts (51.0%) of cis-[[2,4-difluorophenyl)-2-(1H-1,2,4-triazol-1-ylmethyl)-1,3-dioxolan-4-yl]methyl]-2-naphthalenesulfonate; mp. 139.5° C. (intermediate 6).

EXAMPLE 3

(a) A mixture of 9.0 parts of 4-[4-(4-nitrophenyl)-1-piperazinyl]phenol, 13.6 parts of cis-2-(2,4-difluorophenyl)-2-(1H-1,2,4-triazol-1-ylmethyl)-1,3-dioxolane-4-methanol methanesulfonate(ester), 6.0 parts of potassium hydroxide and 90 parts of N,N-dimethylformamide was stirred overnight at 70° C. under nitrogen atmosphere. After cooling, the reaction mixture was diluted with water. The precipitated product was filtered off and purified by column chromatography over silica gel using a mixture of trichloromethane, ethyl acetate, hexane and methanol (500:300:200:0.5 by volume) as eluent. The pure fractions were collected and the eluent was evaporated. The residue was crystallized from 4-methyl-2-pentanone. The product was filtered off and dried, yielding 6.69 parts (38.5%) of cis-1-[4-[[2-(2,4-difluorophenyl)-2-(1H-1,2,4-triazol-1ylmethyl)-1,3-dioxolan-4-yl]methoxy]-phenyl]-4-(4-nitrophenyl)piperazine; mp. 169.8° C. (intermediate 7).

(b) A mixture of 38.3 parts of cis-1-[4-[[2-(2,4-difluorophenyl)-2-(1H-1,2,4-triazol-1-ylmethyl)-1,3-dioxolan-4-yl]methoxy]phenyl]-4-(4-nitrophenyl)piperazine, 2 parts of a solution of thiophene in methanol 4% and 600 parts of 2-methoxyethanol was hydrogenated at normal pressure and at 50° C. with 2 parts of platinum-on-charcoal catalyst 5%. After the calculated amount of hydrogen was taken up, the catalyst was filtered off while hot and the filtrate was saturated with water. After cooling, the precipitated product was filtered off, washed with water and 2-propanol and crystallized from 1,4-dioxane. The product was filtered off and dried, yielding 22.7 parts (62.6%) of cis-4-[4-[[2-(2,4-difluorophenyl)-2-(1H-1,2,4-triazol-1-ylmethyl)-1,3-dioxolan-4-yl]methoxy]phenyl]-1-piperazinyl]benzenamine; mp. 193.0° C. (intermediate 8).

EXAMPLE 4

(a) A mixture of 10 parts of 2,4-dihydro-4-[4-[4-(4-methoxyphenyl)-1-piperazinyl]phenyl]-3H-1,2,4-triazol-3-one, prepared as described in Example XVII of U.S. Pat. No. 4,267,179, 1.5 parts of a sodium hydride dispersion 50% and 300 parts of dimethyl sulfoxide was stirred at 60° C. under nitrogen atmosphere till foaming had ceased. Then there were added 5.24 parts of 2-bromopropane and stirring was continued for 1 hour at 60° C. Another 1.5 parts of a sodium hydride dispersion 50% was added and stirring was continued till foaming had ceased. Then another 5.24 parts of 2-bromopropane was aded and the whole was stirred for 1 hour at 60° C. The reaction mixture was cooled and poured into water. The product was extracted with trichloromethane. The extract was washed with water, dried, filtered and evaporated. The residue was purified by column chromatography over silica gel using a mixture of trichloromethane and methanol (99:1 by volume) as eluent. The pure fractions were collected and the eluent was evaporated. The residue was crystallized from 1-butanol, yielding 5.2 parts (47%) of 2,4-dihydro-4-[4-[4-(4-methoxyphenyl)-1-piperazinyl]phenyl]-2-(1-methylethyl)-3H-1,2,4-triazol-3-one; mp. 209.5° C. (intermediate 9).

(b) A mixture of 4.7 parts of 2,4-dihydro-4-[4-[4-(4-methoxyphenyl)-1-piperazinyl]phenyl]-2-(1-methylethyl)-3H-1,2,4-triazol-3-one and 75 parts of a hydrobromic acid solution 48% in water was stirred and refluxed for 3 hours. The reaction mixture was evaporated and the residue was dissolved in a mixture of methanol and water. The whole was neutralized with a sodium hydrogen carbonate solution and the product was extracted with trichloromethane. The extract was dried, filtered and evaporated. The residue was triturated in 2-propanol, yielding 3.9 parts (86%) of 2,4-dihydro-4-[4-[4-(4-hydroxyphenyl)-1-piperazinyl]phenyl]-2-(1-methylethyl)-3H-1,2,4-triazol-3-one, mp. 208.4° C. (intermediate 10).

In a similar manner there were also prepared: 2,4-dihydro-4-[4-[4-(4-hydroxyphenyl)-1-piperazinyl]phenyl]-2-(1-methylpropyl)-3H-1,2,4-triazol-3-one; mp. 187.6° C. (intermediate 11); 2,4-dihydro-4-[4-[4-(4-hydroxyphenyl)-1-piperazinyl]phenyl]-2-(3-methylbutyl)-3H-1,2,4-triazol-3-one; mp. 216.6° C. (intermediate 12); 2,4-dihydro-4-[4-[4-(4-hydroxyphenyl)-1-piperazinyl]phenyl]-5-methyl-2-(1-methylpropyl)-3H-1,2,4-triazol-3-one; mp. 239.9° C. (intermediate 13); 2,4-dihydro-4-[4-[4-(4-hydroxyphenyl)-1-piperazinyl]phenyl]-2-propyl-3H-1,2,4-triazol-3-one as a solid residue (intermediate 14); 2-ethyl-2,4-dihydro-4-[4-[4-(4-hydroxyphenyl)-1-piperazinyl]phenyl]-3H-1,2,4-triazol-3-one; mp. 217° C. (intermediate 15); and 2,4-dihydro-4-[4-[4-(4-hydroxyphenyl)-1-piperazinyl]phenyl]-2-pentyl-3H-1,2,4-triazol-3-one; mp. 202.1° C. (intermediate 16).

B. Preparation of final compounds

EXAMPLE 5

(a) A mixture of 9.8 parts of 2,4-dihydro-4-[4-[4-(4-hydroxyphenyl)-1-piperazinyl]phenyl]-2-(1-methylpropyl)-3H-1,2,4-triazol-3-one, 12 parts of cis-2-(2,4-difluorophenyl)-2-(1H-1,2,4-triazol-1-ylmethyl)-1,3-dioxolane-4-methanol methanesulfonate(ester), 4.2 parts of potassium hydroxide and 135 parts of N,N-dimethylformanide was stirred and heated for 2 hours at 60° C. under nitrogen atmosphere. The reaction mixture was evaporated. The residue was taken up in water. The product was filtered off and taken up in trichloromethane. The organic layer was dried, filtered and evaporated. The residue was crystallized from acetonitrile. The product was filtered off and dried, yielding 12.8 parts (76.1%) of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 189.5° C. (compound 1).

In a similar manner there were also prepared: cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylethyl)-3H-1,2,4-triazol-3-one; mp. 211.1° C. (compound 2); and cis-4-[4-[4-[4-[[2-(2,4-difluorophenyl)-2-(1H-imidazol-1-ylmethyl)-1,3-dioxolan-4-yl]methoxy]phenyl]-1-piperazinyl]phenyl]-2,4-dihydro-2-(1-methylethyl)-3H-1,2,4-triazol-3-one; mp. 218.8° C. (compound 3).

(b) To a stirred solution of 6.8 parts of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one in 80 parts of 2-propanone were added 3.2 parts of methanesulfonic acid. After the addition of 73 parts of 2,2'-oxybispropane, the crystallized product was filtered off and recrystallized from a mixture of acetonitrile and 2,2'-oxybispropane. The product was filtered off and dried, yielding 8.4 parts (92.0%) of cis-4-[4-[4-[[2-(2,4-difluorophenyl)-2H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one methanesulfonate (2:5); mp. 151.7° C. (compound 4).

EXAMPLE 6

A mixture of 4 parts of 2,4-dihydro-4-[4-[4-(4-hydroxyphenyl)-1-piperazinyl]phenyl]-5-methyl-2-(1-methylpropyl)-3H-1,2,4-triazol-3-one, 5.6 parts of cis-[[2-(2,4-difluorophenyl)-2-(1H-1,2,4-triazol-1-ylmethyl)-1,3-dioxolan-4-yl]methyl]-2-naphthalenesulfonate, 1 part of sodium hydroxide pellets and 90 parts of N,N-dimethylformamide was stirred for 4 hours at 60° C. under nitrogen atmosphere. 300 Parts of water were added. The precipitated product was filtered off, washed with water and purified by column chromatography over silica gel using a mixture of trichloromethane and methanol (99:1 by volume) as eluent. The pure fractions were collected and the eluent was evaporated. The residue was crystallized from 2-propanol. The product was filtered off and dried, yielding 4.7 parts (68.4%) of cis-4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2,4-dihydro-5-methyl-2-(1-methylpropyl)-3H-1,2,4-triazol-3-one; mp. 157.2° C. (compound 5).

In a similar manner there were also prepared: cis-4-[4-[4-[[2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(3H-1,2,4-triazol-3-one; mp. 181.6° C. (compound 6); cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-propyl-3H-1,2,4-triazol-3-one; mp. 178.2° C. (compound 7); and cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-ethyl-2,4-dihydro-3H-1,2,4-triazol-3-one; mp. 186.9° C. (compound 8).

EXAMPLE 7

A mixture of 8.1 parts of 2,4-dihydro-4-[4-[4-(4-hydroxyphenyl)-1-piperazinyl]phenyl]-2-(3-methylbutyl)-3H-1,2,4-triazol-3-one, 10 parts of cis-2-(2,4-difluorophenyl)-2-(1H-imidazol-1-ylmethyl)-1,3-dioxolane-4-methanol methanesulfonate(ester) monohydrochloride, 3 parts of sodium hydroxide and 90 parts N,N-dimethylformamide was stirred for 8 hours at 70° C. under nitrogen atmosphere. After the addition of 200 parts of water, the precipitated product was filtered off, washed with water and 2-propanol and purified by column chromatography over silica gel, first using a mixture of trichloromethane and methanol (99.5:0.5 by volume) and then a mixture of trichloromethane, ethyl acetate, hexane and methanol (45:30:20:5 by volume) as eluents. The pure fractions were collected and the eluent was evaporated. The residue was crystallized from 4-methyl-2-pentanone. The product was filtered off and dried, yielding 10.5 parts (76%) of cis-4-[4-[4-[4-[[2-(2,4-difluorophenyl)-2-(1H-imidazol-1-ylmethyl)-1,3-dioxolan-4-yl]methoxy]phenyl]-1-piperazinyl]phenyl]-2,4-dihydro-2-(3-methylbutyl)-3H-1,2,4-triazol-3-one; mp. 205.0° C. (compound 9).

In a similar manner there were also prepared: cis-4-[4-[4-[4-[[2-(2,4-difluorophenyl)-2-(1H-imidazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 180.5° C. (compound 10); and cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-pentyl-3H-1,2,4-triazol-3-one; mp. 172.8° C. (compound 11).

EXAMPLE 8

A mixture of 7.6 parts of 1,2-dimethylpropanol methanesulfonate (ester), 5 parts of cis-4-[4-[4-[4-[[2-(2,4-difluorophenyl)-2(1H-1,2,4-triazol-1-ylmethyl)-1,3-dioxolan-4-yl]methoxy]phenyl]-1-piperazinyl]phenyl]-2,4-dihydro-3H-1,2,4-triazol-3-one, 6 parts of potassium carbonate, 90 parts of N,N-dimethylformamide and 135 parts of benzene was stirred at reflux temperature using a water separator. The reaction mixture was concentrated by distilling off the benzene and stirring was continued overnight at reflux temperature. After cooling, the reaction mixture was poured into water and the product was extracted with dichloromethane. The extract was washed with water, dried, filtered and evaporated. The residue was purified by column chromatography over silica gel using a mixture of trichloromethane and methanol (99:1 by volume) as eluent. The pure fractions were collected and the eluent was evaporated. The residue was crystallized from 4-methyl-2-pentanone. The product was filtered off and dried, yielding 2.4 parts (43%) of cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-(1,2-dimethylpropyl)-2,4-dihydro-3H-1,2,4-triazol-3-one; mp. 160.7° C. (compound 12).

EXAMPLE 9

A mixture of 25 parts of ethyl [dimethylamino)methylene]hydrazinecarboxylate, 58 parts of cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]benzenamine and 75.6 parts of tetrahydrothiophene 1,1-dioxide was stirred for 3 hours at 160° C. (oil bath). 80 Parts of 4-methyl-2-pentanone were added. After cooling, the precipitated product was filtered off, washed with 4-methyl-2-pentanone and dried, yielding 46.2 parts (70%) of cis-4-[4-[4-[4-[[2-(2,4-difluorophenyl)-2-(1H-1,2,4-triazol-1-ylmethyl)-1,3-dioxolan-4-yl]methoxy]phenyl[-1-piperazinyl]-phenyl]-2,4-dihydro-3H-1,2,4-triazol-3-one (compound 13).

C. Pharmacological examples

The superior antimicrobial activity of the compounds of formula (I) is clearly evidenced by the data obtained in the following experiments. Said data are supplemented to illsutrate the useful antimicrobial properties of all compounds (I) and not to limit the invention with respect to the scope of susceptible microorganisms nor with respect to the scope of formula (I).

EXAMPLE 10

(a) Topical treatment of vaginal candidosis in rats.

Female Wistar rats of ±100 g body weight were used. They were ovariectomized and hysterectomized and after three weeks of recovery, 100 μg of oestradiol undecylate in sesame oil was given subcutaneously once a week for 3 consecutive weeks. The thus induced pseudooestrus was controlled by microscopic examination of vaginal smears. Food and water were left available ad libitum. The rats were infected intravaginally with $8.10^5$ cells of *Candida albicans*, grown on Sabouraud broth for 48 hours at 37° C. and diluted with saline. The date of infection varied from day +25 to day +32 after surgical intervention, depending on the appearance of signs of inducing pseudo-oestrus. The drugs under investigation were administered topically twice a day for three consecutive days starting from the third day after infection. For each experiment there were placebo treated controls. The results were assessed by taking vaginal smears with sterile swabs on several days after the infection. The swabs were put into Sabouraud broth in petri-dishes and incubated for 48 hours at 37° C. When the animals were negative at the end of the experiment, i.e., if no growth of *Candida albicans* occured, this had to be due to drug administration because placebo-treated controls were always positive. The first column of table I shows the lowest topical concentration of the drug under investigation which was found to be active up to 7 days after the last topical administration of the drug.

(b) Topical treatment of microsporosis in guinea pigs.

Adult Albino guinea pigs were prepared by clipping their backs and infected on the scarified skin by scratching five 3 cm long transverse cuts with *Microsporum canis* (strain RV 14314). The animals were housed individually in wire mesh cages and food and water were available ad libitum. The drugs under investigantion were administered topically once a day for 14 consecutive days starting the third day after infection. For each experiment there were placebo treated controls.

The animals were evaluated 21 days after infection by microscopic examination of the skin and by cultures on Sabouraud agar comprising a suitable bacterial antibiotic and a suitable agent to eliminate contaminating fungi.

The second column of table I contains the lowest topical concentration (%) of the drug under investigation at which no lesions were observed and at which there was no culture growth.

TABLE I

| Comp. No. | Vaginal candidosis in rats lowest topical concentration | Microsporosis in rats lowest topical concentration |
| --- | --- | --- |
| 1 | ~0.05 | 0.031 |
| 2 | 0.016 | 0.063 |
| 4 | 0.016 | ~0.063 |
| 6 | 0.031 | ~0.063 |
| 12 | 0.031 | ~0.063 |

EXAMPLE 11

Oral treatment of aspergillosis in mice

Swiss mice weighing 23 to 27 g were infected with *Aspergillus fumigatus* as described in Antimicrob. Agents Chemother., 1984, 26, 527–534. The amimals were treated by gavage with either the solvent (polyethylene glycol 200) or with a compound of formula (I) in polyethylene glycol 200 at 2.5, 1.25 and 0.63 mg/kg o.d. (oral dose) for 5 consecutive days, starting on the day of infection. The first treatment was given immediately before the infection. The animals were observed for 28 days and drug efficacy was evaluated in terms of mean survial time in days. Solvent-treatment animals, infected with *A. funigatus* and serving as controls, had a mean survial time of 5.33 days.

The mean survival time for some compounds of the present invention and for cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one, which compound is generically designated as itraconazole and is described in U.S. Pat. No. 4,267,179, can be found in table II.

From these values it can be concluded that the compounds of the present invention are superior over the prior art compound.

TABLE II

| Compound No. | mean survival time (days) | | |
|---|---|---|---|
| | o.d 2.5 mg/kg | o.d. 1.25 mg/kg | o.d. 0.63 mg/kg |
| * | 15.6 | 7.0 | 5.8 |
| 1 | ≧28 | 25.3 | 10.9 |
| 6 | ≧28 | 18 | 12.8 |
| 12 | — | ≧28 | 21.5 |

* = itraconazole

D. Composition Examples

The following formulations exemplify typical pharmaceutical compositions in dosage unit form suitable for systemic administration to animal and human subjects in accordance with the instant invention. "Active ingredient" (A.I.) as used throughout these examples relates to a compound of formula (I) or a pharmaceutically acceptable acid addition salt thereof.

EXAMPLE 12

Oral Drops

500 Grams of the A.I. was dissolved in 0.5 liters of 2-hydroxypropanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution containing 10 milligrams of the A.I. per milliliter. The resulting solution was filled into suitable containers.

EXAMPLE 13

Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution containing 20 milligrams of the active ingredient per teaspoonful (5 milliliters). The resulting solution was filled in suitable containers.

EXAMPLE 14

Capsules

20 Grams of the A.I., 6 sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable, hardened gelatin capsules, comprising each 20 milligrams of the active ingredient.

EXAMPLE 15

Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed welll and compressed into tablets, giving 10,000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

EXAMPLE 16

Injectable Solution 1.8 Grams methyl 4-hydroxybenzoate and 0.2 grams propyl 4-hydroxybenzoate were dissolved in about 0.5 liters of boiling water for injection. After cooling to about 50 C. there were added while stirring 4 grams lactic acid, 0.05 grams propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 17

Suppositories

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°~38° C. to form 100 suppositories each containing 30 milligrams of the A.I.

What is claimed is:

1. A compound of the formula:

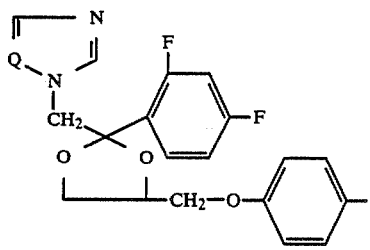

(I)

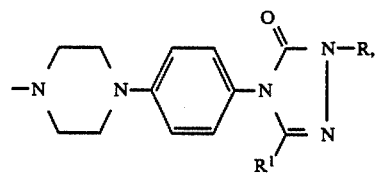

a pharmaceutically acceptable acid-addition salt or a stereochemically isomeric form thereof, wherein:
the substituents on the dioxolane moiety have a cis configuration;
Q is N or CH; and
R is $C_{1-6}$alkyl and $R^1$ is hydrogen.

2. A compound according to claim 1 wherein Q is nitrogen.

3. A compound according to claim 1 wherein the compound is cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one.

4. A compound according to claim 1 wherein the compound is cis-4-[4-[4-[4-[[2-(2,4-difluorophenyl)-2-(1H-1,2,4-triazol-1-ylmethyl)-1,3-dioxolan-4-yl]-methoxy]phenyl]-1-piperazinyl]phenyl]-2-(1,2-dimethylpropyl)-2,4-dihydro-3H-1,2,4-triazol-3-one.

5. An antimicrobial composition comprising one or more inert carriers and as active ingredient an antimicrobially effective amount of a compound as claimed in claim 1.

6. A composition according to claim 5 wherein Q is nitrogen.

7. A composition according to claim 5 wherein the compound is cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2(1-methylpropyl)-3H-1,2,4-triazol-3-one, or cis-4-[4-[4-[4-[[2(2,4-difluorophenyl)-2-(1H-1,2,4-triazol-1-ylmethyl)-1,3-dioxolan-4-yl]methoxy]phenyl]-1-piperazinyl]-phenyl]-2-(1,2-dimethylpropyl)-2,4-dihydro-3H-1,2,4-triazol-3-one.

8. A method of inhibiting and/or eliminating the development of fungi and bacteria in warm-blooded animals suffering from diseases caused by these fungi and/or bacteria by the systemic or topical administration to said warm-blooded animals of an antimicrobially effective amount of a compound as claimed in claim 1.

9. A method according to claim 8 wherein Q is nitrogen.

10. A method according to claim 8 wherein the compound is cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one, or cis-4-[4-[4-[4-[[2-(2,4-difluorophenyl)-2-(1H-1,2,4-triazol-1-ylmethyl)-1,3-dioxolan-4-yl]methoxy]phenyl]-2-(1,2-dimethylpropyl)-2,4-dihydro-3H-1,2,4-triazol-3-one.

* * * * *